US00PP20664P2

(12) United States Plant Patent
van der Knaap

(10) Patent No.: US PP20,664 P2
(45) Date of Patent: Jan. 19, 2010

(54) *CURCUMA* PLANT NAMED 'CURDJENNA'

(50) Latin Name: *Curcuma alismatifolia*
Varietal Denomination: Curdjenna

(75) Inventor: Leonardus Johannus Maria van der Knaap, Naaldwijk (NL)

(73) Assignee: Knaao Licenties B.V., Naaldwijk (NL)

( * ) Notice: Subject to any disclaimer, the term of this patent is extended or adjusted under 35 U.S.C. 154(b) by 0 days.

(21) Appl. No.: 12/287,360

(22) Filed: Oct. 8, 2008

(51) Int. Cl.
*A01H 5/00* (2006.01)

(52) U.S. Cl. ..... Plt./421

(58) Field of Classification Search ..... Plt./421
See application file for complete search history.

*Primary Examiner*—Kent L Bell
(74) *Attorney, Agent, or Firm*—C. A. Whealy

(57) ABSTRACT

A new and distinct cultivar of *Curcuma* plant named 'Curdjenna', characterized by its compact, upright and columnar plant habit with outwardly arching leaves; freely clumping growth habit; medium green-colored leaves; flowers with pink-colored flower bracts that are positioned just above the foliage on strong and erect peduncles; and freely flowering habit.

2 Drawing Sheets

Botanical designation: *Curcuma alismatifolia.*
Cultivar denomination: 'Curdjenna'.

BACKGROUND OF THE INVENTION

The present invention relates to a new and distinct cultivar of *Curcuma* plant, botanically known as *Curcuma alismatifolia* and hereinafter referred to by the name 'Curdjenna'.

The new *Curcuma* plant is a product of a controlled breeding program conducted by the Inventor in De Lier, The Netherlands. The objective of the breeding program is to create new *Curcumas* that have uniform plant habit, good container performance and attractive inflorescence coloration.

The new *Curcuma* plant originated from a cross-pollination made by the Inventor on May 24, 2004, in De Lier, The Netherlands of a proprietary selection of *Curcuma alismatifolia* identified as code number 20000958-002, not patented, as the female, or seed, parent with a proprietary selection of *Curcuma alismatifolia* identified as code number 20000816-001, not patented, as the male, or pollen, parent. The new *Curcuma* was discovered and selected by the Inventor as a single flowering plant within the progeny of the stated cross-pollination in a controlled greenhouse environment in De Lier, The Netherlands on Jun. 5, 2006.

Asexual reproduction of the new *Curcuma* plant by tissue culture in a controlled environment in Maasdijk, The Netherlands since Jun. 5, 2006 has shown that the unique features of this new *Curcuma* are stable and reproduced true to type in successive generations of asexual reproduction.

SUMMARY OF THE INVENTION

Plants of the new *Curcuma* have not been observed under all possible environmental conditions. The phenotype may vary somewhat with variations in environment such as temperature and light intensity, without, however, any variance in genotype.

The following traits have been repeatedly observed and are determined to be the unique characteristics of 'Curdjenna'. These characteristics in combination distinguish 'Curdjenna' as a new and distinct cultivar of *Curcuma:*

1. Compact, upright and columnar plant habit with outwardly arching leaves.
2. Freely clumping growth habit.

3. Medium green-colored leaves.
4. Flowers with pink-colored flower bracts that are positioned just above the foliage on strong and erect peduncles.
5. Freely flowering habit.

Plants of the new *Curcuma* differ from plants of the female parent selection in the following characteristics:

1. Plants of the new *Curcuma* are more compact than plants of the female parent selection.
2. Plants of the new *Curcuma* have smaller leaves than plants of the female parent selection.
3. Plants of the new *Curcuma* and the female parent selection differ in flower bract color as plants of the female parent selection have flower bracts with lighter pink-colored apices.

Plants of the new *Curcuma* differ from plants of the male parent selection in the following characteristics:

1. Plants of the new *Curcuma* are more freely clumping than plants of the male parent selection.
2. Plants of the new *Curcuma* and the male parent selection differ in flower bract color as plants of the male parent selection have light pink-colored flower bracts.

Plants of the new *Curcuma* can also be compared to plants of *Curcuma alismatifolia* 'Curzena', disclosed in U.S. Plant Pat. No. 19,956. In side-by-side comparisons conducted in De Lier, The Netherlands, plants of the new *Curcuma* differed from plants of 'Curzena' in the following characteristics:

1. Plants of the new *Curcuma* were more compact than plants of 'Curzena'.
2. Plants of the new *Curcuma* were more freely flowering than plants of 'Curzena'.
3. Plants of the new *Curcuma* and 'Curzena' differed in flower bract color as plants of 'Curzena' had light pink-colored flower bracts.

BRIEF DESCRIPTION OF THE PHOTOGRAPHS

The accompanying photographs illustrate the overall appearance of the new *Curcuma.* These photographs show the colors as true as it is reasonably possible to obtain in colored reproductions of this type. Colors in the photographs may differ slightly from the color values cited in the detailed botanical description which accurately describe the colors of the new *Curcuma*.

The photograph on the first sheet is a side perspective view of a typical plant of 'Curdjenna' grown in a container.

The photograph on the second sheet is a close-up view of a typical inflorescence of 'Curdjenna'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in 19-cm containers in De Lier, The Netherlands during the summer in a glass-covered greenhouse. Plants were grown under conditions and practices which approximate those generally used in commercial *Curcuma* production. During the production of the plants, day temperatures ranged from about 19° C. to 28° C., night temperatures ranged from about 19° C. to 22° C. and light levels were about 55,000 lux. Plants had been growing for 20 weeks when the photographs and the detailed description were taken.

Botanical classification: *Curcuma alismatifolia* 'Curdjenna'.

Parentage:

*Female, or seed, parent.*—Proprietary selection of *Curcuma alismatifolia* identified as code number 20000958-002, not patented.

*Male, or pollen, parent.*—Proprietary selection of *Curcuma alismatifolia* identified as code number 20000816-001, not patented.

Propagation:

*Type.*—By tissue culture of meristems or by rhizome divisions.

*From tissue culture, time to initiate roots.*—About ten days at 23° C.

*From tissue culture, time to produce a rooted young plant.*—About 28 to 30 days at 21° C.

*Root description.*—Medium in thickness, slightly fleshy; close to 155D in color.

*Rooting habit.*—Moderately branching, moderately dense.

*Number of rhizomes produced per plant.*—About seven.

*Rhizome diameter.*—About 5 mm.

Plant description:

*Growth habit.*—Compact; upright and columnar with outwardly arching leaves; freely clumping habit.

*Plant height (soil level to top of inflorescences).*—About 55.1 cm.

*Plant height (soil level to top of foliar plane).*—About 52.9 cm.

*Foliage description.*—Leaf arrangement: Alternate; simple. Length, fully expanded: About 53.8 cm. Width, fully expanded: About 4.6 cm. Shape: Ligulate. Apex: Acuminate. Base: Sheathing; wings, about 18.8 cm in length. Margin: Entire. Venation: Parallel. Aspect: Initially upright, then outwardly arching. Texture: Smooth, glabrous. Color: Developing and fully expanded leaves, upper surface: Close to N138B; venation, close to 137B to 137C. Developing and fully expanded leaves, lower surface: Between 137B and N138B; venation, close to N138C.

Inflorescence description:

*Arrangement.*—Terminal spike inflorescences develop directly from the rhizome with numerous bracts and bracteole flowers in bract axils.

*Time to flower.*—In The Netherlands, plants flower from spring to autumn; flowering continuous during this period.

*Flower longevity.*—Flowers last about three days on the plant; flowers not persistent.

*Fragrance.*—None detected.

*Inflorescence length.*—About 11.8 cm.

*Inflorescence diameter.*—About 7.1 cm.

*Flowers.*—Length: About 3.5 cm. Diameter: About 1.7 cm. Shape: Zygomorphic with three petals; lower petal (labellum) is conspicuous; calyx with three sepals. Color: Upper two petals and sepals, upper and lower surfaces: Close to 85C; towards the base, close to N155A. Lower petal (labellum), upper surface: Between N79A and 83A; towards the base, close to N155A. Lower petal (labellum), lower surface: Close to 83B to 83C; towards the base, close to N155A to N155B.

*Flower bracts.*—Quantity: About 14 per inflorescence. Length, upper bracts: About 6.2 cm. Width, upper bracts: About 3 cm. Length, lower bracts: About 2.7 cm. Width, upper bracts: About 3.9 cm. Shape, upper bracts: Ovate; apex, acute; base, cuneate; margins, entire. Shape, lower bracts: Reniform to orbicular; apex, obtuse; base, cuneate; margins, entire. Texture, upper and lower surfaces: Smooth, glabrous; waxy. Color: Upper bracts, upper and lower surfaces: Close to N74C; towards the apex, close to 146A to 146B. Lower bracts, upper surface: Close to 144B; towards the base, close to 146D. Lower bracts, lower surface: Close to 144A; towards the base, close to 145A.

*Peduncle.*—Length: About 41 cm. Diameter: About 4 mm. Texture: Smooth, glabrous. Angle: Upright, erect. Color: Close to 143A.

*Stamens.*—Quantity: Two per flower. Filament: Length: About 7 mm. Diameter: About 2 mm. Color: Close to 155D; towards the apex, close to 85C. Anther color: Close to 155D. Pollen amount: Sparse. Pollen color: Close to 155C.

*Pistils.*—Quantity per flower: One. Pistil length: About 3.2 cm. Stigma: Length: About 2 mm. Diameter: About 1 mm. Color: Close to N155A. Style: Length: About 3 cm. Diameter: About 0.2 mm. Color: Close to N155A.

*Seeds/fruits.*—Seed and fruit development have not been observed on plants of the new *Curcuma*.

Disease/pest resistance: Plants of the new *Curcuma* have not been observed to be resistant to pathogens or pests common to *Curcuma*.

Temperature tolerance: Plants of the new *Curcuma* have been observed to be tolerant to temperatures ranging from about 16° C. to about 30° C.

It is claimed:

1. A new and distinct *Curcuma* plant named 'Curdjenna' as illustrated and described.

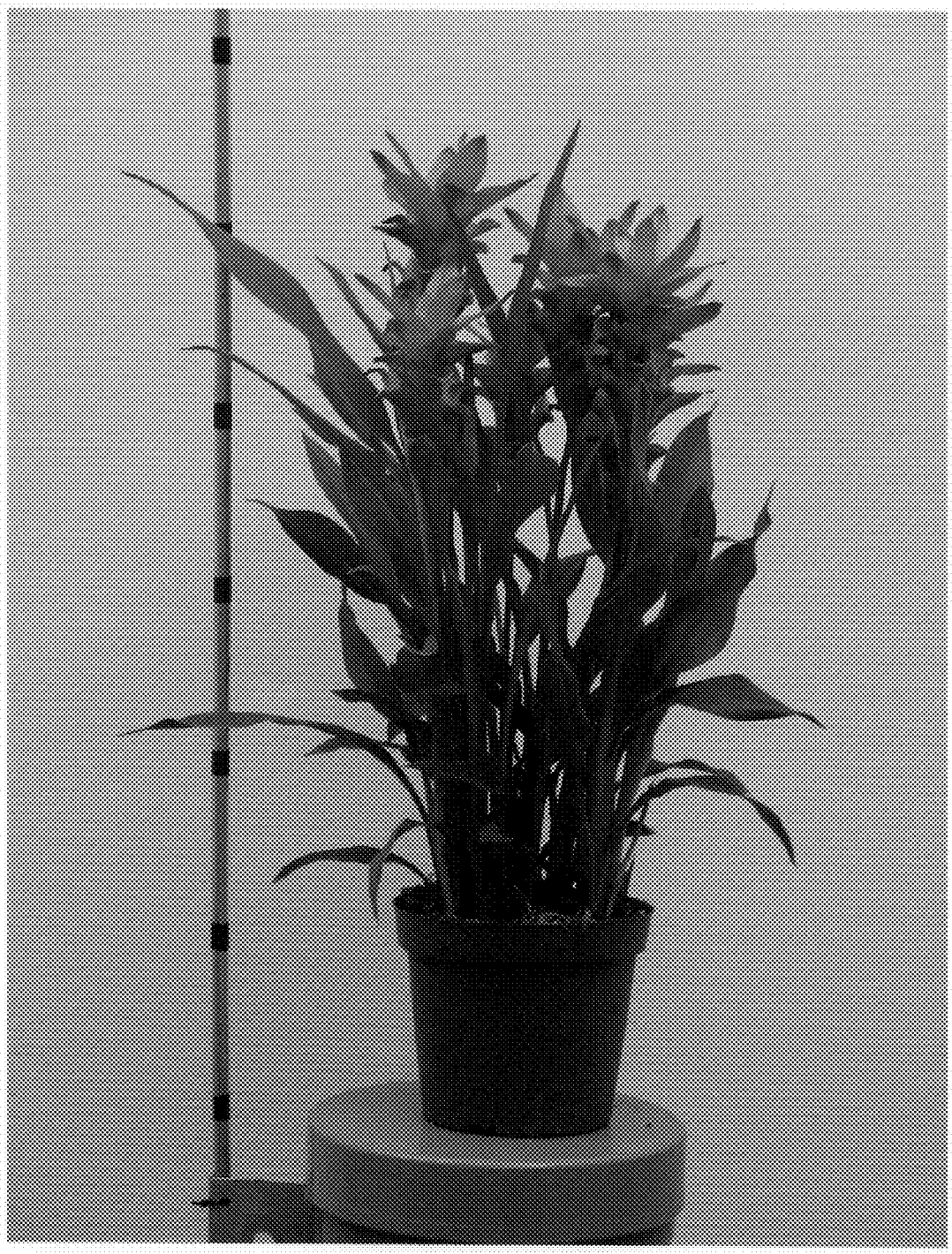

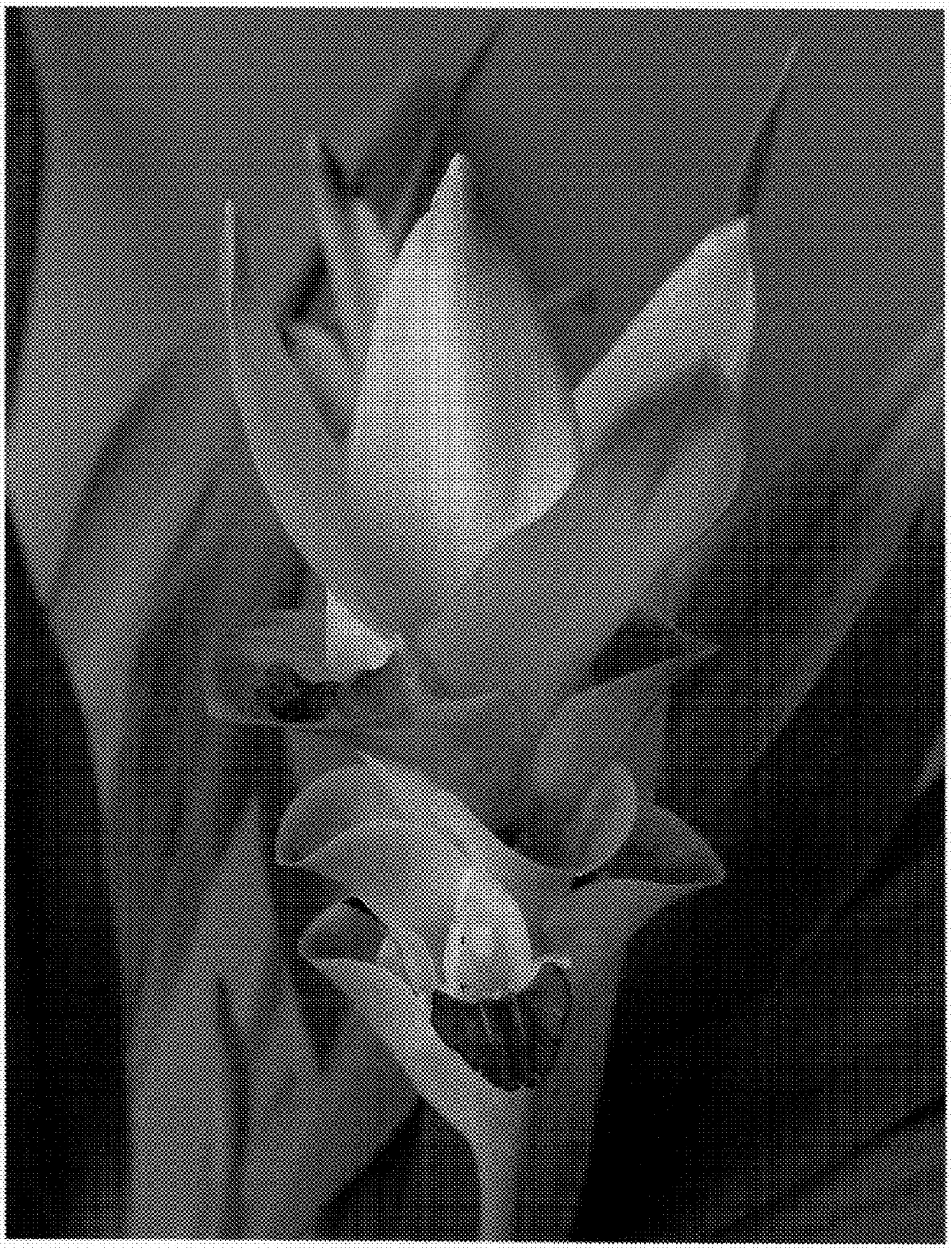

* * * * *